United States Patent [19]

Holtkamp, Sr.

[11] Patent Number: Plant 6,846

[45] Date of Patent: Jun. 13, 1989

[54] AFRICAN VIOLET PLANT NAMED ANGELICA

[76] Inventor: Reinhold Holtkamp, Sr., Werther Strasse 112, D4294 Isselburg, Fed. Rep. of Germany

[21] Appl. No.: 152,816

[22] Filed: Feb. 5, 1988

[51] Int. Cl.[4] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Angelica which is a sport of Indiana, disclosed in U.S. Plant Pat. No. 4,296. Angelica is characterized by its single, shiny, light salmon pink flowers with darker pink center radiating into the 2 small petals; strong, upright flower stems that curve slightly toward the center to form a bouquet above the leaves; bright green, oval to heart-shaped leaves; profuse flowering, vigorous growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Angelica.

The new cultivar was referred to during the breeding and selection process by the designation M of C 165/9-40/77, and is a sport of Indiana, disclosed in my U.S. Plant Pat. No. 4,296 granted in 1978. Angelica is similar in all essential respects to Indiana except for its light salmon pink flower color.

Angelica was discovered in a flowering block of the parent cultivar Indiana, and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Angelica has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Angelica, which in combination distinguish this African violet as a new and distinct cultivar:

(1) Strong, upright flower stems curving slightly toward the center.

(2) Shiny, light salmon pink single flowers.

(3) Profuse flowering.

(4) Each plant carries 8 and more upright flower stems, each of which carries 8–12 flowers.

5) Long lasting, non-dropping flowers.

(6) Vigorous grower.

(7) Plant saleable 10 to 11 weeks after potting.

(8) Seed capsules push slightly through.

(9) Bright green, oval to heart-shaped leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 2 p.m. in Nashville, Tenn.

Botanical Classification: *Saintpaulia ionantha,* Ramt., c.v. Angelica.

Parentage: Sport of Indiana, disclosed in U.S. Plant Pat. No. 4,296.

Propagation: The new cultivar holds its distinguishing characteristics through successive propagations by leaf cuttings.

Plant: From 9 cm to 10 cm tall when grown in pots, and approximately 23–26 cm in diameter when fully grown.

*Leaves.*—General form: Oval to heart-shaped. Diameter: 70–80 mm. Texture: Velvety. Aspect: shiny, hairy. Veins: Upperside: visible; underside: very well pronounced, light green with reddish touch towards the center; on young leaves reddich purple. Color (upperside): Yellow-Green Group 147 A. Color (underside): Greyed-Green Group 194 C. Petiole: Strong upright, reddish brown, greenish on side towards the pot, hairy.

*Flowers.*—Buds: Ball-shaped, 8–9 mm just before opening, light pink. Sepals: Five (5). Color: Green with reddish brown touch. Calyx: Shape: Funnel-shaped. Aspect: Spear-shaped, hairy. Peduncle: Character: Strong upright, hairy. Color: Reddish brown. Individual flowers: Size: 35–45 mm. Shape: Single violet-shaped (3 large and 2 small petals). Color (upperside): Red-Purple Group 62 between C and D. Under cooler temperature and more intensive lighting, the pink tends to intensify. Color (underside): Red-Purple Group 62 between C and D. Borne: Each flower stem carries 8–12 flowers on strong, upright peduncle that are free standing above the leaves, thereby forming a compact bouquet.

Flowering habit: Flowers 10–11 weeks after potting.

*Reproductive organs.*—Stamens: Two (2). Anthers: 2 composed of 4 anther cells, seed capsule pushes slightly through. Filaments: Yellowish green with pink traces, 4 mm long. Pollen Color: Yellow Group 7 A. Styles: 7–8 mm long, pink, base of ovary light green and hairy.

*Roots.*—Normally developed, white when young, turning slightly brownish when older.

Disease resistance: Good.

General observations: Angelica is a vigorous grower with attractive bright green, shiny leaves. A tight bouquet of flowers free standing above the leaves develops after approximately 10–11 weeks. Each of the 8 and more flowers stems carries 8–12 and more shiny, light salmon pink flowers. The single, violet-shaped flowers display a darker pink in the center that radiates into the two smaller petals. Occasionally, 1–2 additional small petals may develop. The flowers are long-lasting and non-dropping and the seed capsule pushes slightly through.

I claim:

1. A new and distinct cultivar of African violet named Angelica, as described and illustrated, and particularly characterized by its single, shiny, light salmon pink flowers with darker pink center radiating into the 2 small petals; strong, upright flower stems that curve slightly toward the center to form a bouquet above the leaves; bright green oval to heart-shaped leaves; profuse flowering, vigorous growth habit, flowering 10–11 weeks after potting, and its long-lasting and non-dropping flowers.

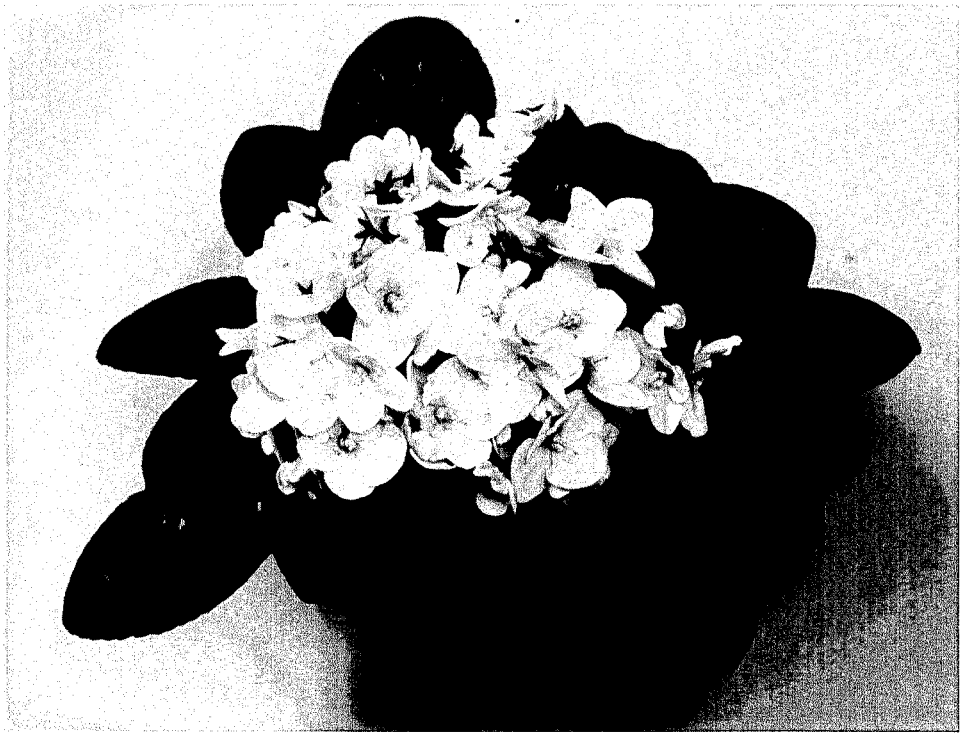

* * * * *